United States Patent
Mommaerts (10) Patent No.: US 10,449,017 B2
(45) Date of Patent: Oct. 22, 2019

(54) SUBPERIOSTEAL JAW IMPLANT

(71) Applicant: CADSKILLS BVBA, Sint-Martens Latem (BE)

(72) Inventor: Maurice Yves Mommaerts, Sint-Martens Latem (BE)

(73) Assignee: CADSKILLS BVBA, Sint-Martens Latem (BE)

( * ) Notice: Subject to any disclaimer, the term of this patent is extended or adjusted under 35 U.S.C. 154(b) by 0 days.

(21) Appl. No.: 15/580,635

(22) PCT Filed: Jun. 6, 2016

(86) PCT No.: PCT/IB2016/000762
§ 371 (c)(1),
(2) Date: Dec. 7, 2017

(87) PCT Pub. No.: WO2016/198935
PCT Pub. Date: Dec. 15, 2016

(65) Prior Publication Data
US 2018/0161129 A1    Jun. 14, 2018

(30) Foreign Application Priority Data

Jun. 8, 2015  (NL) .................................... 1041343
Nov. 6, 2015  (NL) .................................... 1041558

(51) Int. Cl.
A61C 8/00     (2006.01)
B33Y 50/00    (2015.01)
B33Y 80/00    (2015.01)

(52) U.S. Cl.
CPC .......... *A61C 8/0031* (2013.01); *A61C 8/0012* (2013.01); *B33Y 50/00* (2014.12); *B33Y 80/00* (2014.12)

(58) Field of Classification Search
CPC ............................. A61C 8/0031; A61C 8/0039
See application file for complete search history.

(56) References Cited

U.S. PATENT DOCUMENTS

| | | |
|---|---|---|
| 3,577,853 A | 5/1971 | Roberts |
| 3,908,269 A | 9/1975 | Christenot et al. |
| 4,379,694 A | 4/1983 | Riess |
| 4,741,698 A | 5/1988 | Andrews |
| 4,756,690 A | 7/1988 | Roberts |

(Continued)

FOREIGN PATENT DOCUMENTS

| | | |
|---|---|---|
| CA | 2915531 A1 | 1/2015 |
| DE | 1020439 B | 12/1957 |

(Continued)

OTHER PUBLICATIONS

European Communication pursuant to Article 94(3) EPC, dated Dec. 18, 2018, from corresponding EP application No. 16 741 123.0.

(Continued)

*Primary Examiner* — Ralph A Lewis
(74) *Attorney, Agent, or Firm* — Young & Thompson (57) ABSTRACT

In a jaw implant for oral, subperiosteal placement over the alveolar ridge of the maxilla or of the mandible, the implant forms a body which in cross-section, in the condition in which it has been placed on the alveolar ridge transverse to the alveolar ridge, has been formed concave towards the alveolar ridge, wherein in or near a first portion forming the base of the body, in particular forming the base of the J, L or U, the body has been provided with one or more supporting areas for support members, such as pillars, for extending through the gingiva, the support members forming a support for an exo-prosthesis, wherein the supporting areas have been connected to the rest of the body via relatively weakened areas of the body, in particular have been connected to the rest of the body via those relatively weakened areas of the body only.

20 Claims, 5 Drawing Sheets

(56) References Cited

U.S. PATENT DOCUMENTS

| | | | | |
|---|---|---|---|---|
| 5,052,930 | A * | 10/1991 | Lodde | A61C 8/0031 433/173 |
| 5,769,637 | A | 6/1998 | Morgan | |
| 6,030,218 | A | 2/2000 | Robinson | |
| 8,202,089 | B2 * | 6/2012 | Dacremont | A61C 8/0031 433/173 |
| 2007/0269769 | A1 | 11/2007 | Marchesi | |
| 2010/0112522 | A1 * | 5/2010 | Kwon | A61C 8/0031 433/174 |
| 2011/0269100 | A1 | 11/2011 | Furrer et al. | |
| 2012/0064489 | A1 | 3/2012 | Rubbert et al. | |
| 2012/0156645 | A1 * | 6/2012 | Jacoby | A61C 8/0062 433/173 |
| 2013/0164707 | A1 * | 6/2013 | Ali | A61C 8/0027 433/173 |
| 2014/0248583 | A1 | 9/2014 | Rostami | |
| 2016/0022385 | A1 | 1/2016 | Zhao | |
| 2016/0302892 | A1 * | 10/2016 | Almogahwi | A61C 8/0031 |
| 2018/0104028 | A1 * | 4/2018 | Robichaud | A61C 8/0027 |

FOREIGN PATENT DOCUMENTS

| | | |
|---|---|---|
| DE | 3302758 A1 | 8/1983 |
| DE | 20 2015 001 579 U1 | 5/2015 |
| FR | 2 522 495 A1 | 9/1983 |
| GB | 770 696 A | 3/1957 |
| RU | 2 317 794 C1 | 2/2008 |
| WO | 02/39921 A1 | 5/2002 |
| WO | 2013/096592 A1 | 6/2013 |

OTHER PUBLICATIONS

Zigang Ge et al., "Histological evaluation of osteogenesis of 3D-printed poly-lactic-co-glycolic acid (PLGA) scaffolds in a rabbit model", Biomedical Materials, 2009, vol. 4, No. 2.

Dentsply International, "Atlantis-™ ISUS patient-specific suprastructures Beyond CAD/CAM", 2014.

Madhav et al., "Rapid Prototyping and its Application in Dentistry", Journal of Dental & Allied Sciences, 2013, pp. 57-61, vol. 2, No. 2.

Linkow, Historical Dental Implant Educational Materials (1952-2002), pp. 171-183.

International Search Report, dated Sep. 12, 2016, from corresponding PCT application No. PCT/IB2016/000762.

NL Search Report, dated Jan. 27, 2016, from corresponding NL application No. NL 1041343.

NL Search Report, dated Jun. 23, 2016, from corresponding NL application No. NL 1041558.

* cited by examiner

SUBPERIOSTEAL JAW IMPLANT

BACKGROUND OF THE INVENTION

The invention relates to a subperiosteal jaw implant and to a method for manufacturing such an implant.

The invention relates to an assembly of a jaw implant for oral subperiosteal placement of a dental prosthesis over the alveolar ridge of a patient's maxilla or mandible, and of column-shaped supports for supporting the dentures on the jaw implant. The invention further relates to placing such an assembly.

Subperiosteal implants are used in oral and maxillofacial surgery, including dentistry, when a patient is suffering from partial or complete edentulism or advanced bone atrophy and needs to wear a dental prosthesis. After the jaw bone has temporarily been stripped of the gingiva and mucosa, the implant is attached to the jaw bone that is still present by means of screws. The implant forms an endo-prosthesis, to which, via transmucosal/transgingival supports, usually in the form of columns or pillars, the actual dental prosthesis or dentures, the exo-prosthesis, is attached.

Subperiosteal jaw implants are used if bone grafting, an alveolar ridge augmentation or sinus lift is not an option or inconvenient.

In an old technique (Weinberg) a grid-shaped plate was bent in accordance with the shape of the jaw bone and cut to size and finished. Subsequently a supporting column for the endo-prosthesis was soldered onto the plate situated underneath the bone membrane, which plate was bent on both sides of the alveolar ridge like a saddle. The soft tissue was then placed back again and sutured. The intention was that the plate would follow the contours of the supporting bone and the fit would contribute to the stability. However, this often turned out not to be the case.

Goldberg and Gerhkoff had a different approach, wherein an impression was made of the jaw, over the soft tissue and an estimate of the tissue thickness was made by means of X-rays and palpation, on the basis of which data a plaster model of the jawbone was made. Based on said model a molded piece out of Vitallium (a chromium-cobalt-molybdenum alloy) was made, with support columns thereon, formed as one unity therewith. The tissue on the bone was incised and laid aside, after which the molded piece was placed on the exposed bone and attached thereto using vertical screws. The soft tissue was then sutured again. In this case as well, the stability often turned out inadequate in the long term due to the inaccurate fit and peri-implantitis due to failing gingival-adhesion to the metal.

Berman, Lew, Marziani and others started from an impression of the exposed alveolar ridge for a better fit. Berman made a plaster model in the image of the impression. From the stone model he cast a grid-shaped implant made of Vitallium that was attached using tantalum wires. Marzani made a plaster compression mold from the impression, in which mold a wire mesh or grid-shaped plate made of tantalum was pressed into the right shape. Support columns were soldered or screwed secure to the implant. The implant was then attached to the jaw bone using screws on the exterior inclined areas of the alveolar ridge and on the symphysis.

Making an impression of the alveolar ridge after making an incision into the soft tissue and laying it aside, is very trying for a patient. Furthermore, the long period passing between making the impression and placing the implant during a second surgical session is also onerous.

A further drawback in existing techniques and subperiosteal implants is the problem that in case of failing gingival adhesion, gingivitis may arise around the pillars between the implant and the prosthesis, the gingivitis spreading along the pillar in a direction towards the implant and possibly resulting in peri-implantitis, bone decay, in the area surrounding and underneath the implant. This may result in a bone crater and in case of spreading may cause a perforation towards the sinus, the nose, the canalis mandibularis. Further ingrowing epithelium may result in the entire frame getting detached from the bone.

SUMMARY OF THE INVENTION

It is an object of the invention to provide a subperiosteal jaw implant that causes a patient less inconvenience.

It is an object of the invention to provide a subperiosteal jaw implant with which the adverse effects it involves can be kept within limits.

According to one aspect, the invention provides a jaw implant for oral, subperiosteal placement over the alveolar ridge of the maxilla or of the mandible, wherein the implant forms a body which in cross-section, in the condition in which it has been placed on the alveolar ridge transverse to the alveolar ridge, has been formed concave towards the alveolar ridge, such as J-shaped, L-shaped or U-shaped, like in a kind of full or semi saddle shape, wherein in or near a first portion forming the base of the body, in particular forming the base of the J, L or U, the body has been provided with one or more supporting areas for support members, such as columns or pillars, for extending through the gingiva, in particular passing through it, said supporting areas being integrally formed with the body, said support members forming a support for an exo-prosthesis, such as a dental prosthesis or dentures, with or without replacing the alveolar ridge or part of the basic jaw, wherein the supporting areas have been connected to the rest of the body via relatively weakened areas of the body, in particular have been connected to the rest of the body via those relatively weakened areas of the body only. In that way one or more supporting areas, in particular those bearing one or more columns extending through the soft tissue, near a bone area infected with peri-implantitis can be detached relatively easily from the rest of the body of the implant, and thus also the attached support member, such as the pillar, for the exo-prosthesis, using rotary-driven instruments and/or manually driven instruments. The rest of the implant can remain in its place, thus relatively limiting the inconvenience to the patient. The exo-prosthesis can be placed back again, wherein, if so desired, an open space therein can be closed up, for instance using a screw.

In one embodiment each supporting area has been connected to the rest of the body via its own weakened areas, so that the area to be removed can be kept limited.

In one embodiment, at least at the location of the supporting areas, the body has an open structure, such as a framework or grid, with bars or strips between the holes of the open structure. Material can be saved on because of these holes and they may also form holes through which tissue can grow, as known per se from for instance U.S. Pat. No. 4,379,694 and WO 02/39921. The weakened areas can then remain restricted to within the bars of the grid or framework, forming a part thereof. The holes between the bars or strips are not encompassed by the concept of 'weakened areas'. For instance, a supporting area can be connected to the body by three or four bars with weakened areas.

The weakened areas can be configured in various ways. They may for instance have been formed by porous areas. Adhesion to the bone can then also be enhanced if the porous areas form the lower surface of the weakened area. The pores may have a cross-section that is smaller than 1 mm, for instance in the order of a few tenths of one mm, such as 0.5 mm. The weakened areas may be continuous over the full thickness of the body.

The weakened areas may also have been formed by areas having a relatively reduced wall thickness, such as a smaller thickness due to a slot in the exterior surface or an internal cavity, such as a tube shape. The weakened areas may for instance have been formed by hollow bar sections in the body.

The weakened areas may also have been formed by areas having perforations in the material of the body, for instance a series of holes positioned circumferentially around a supporting area, the holes having a cross-section that is smaller than the thickness of the body at that location. In case of said grid and the like the bars or strips may have been provided with such perforations.

In an advantageous embodiment the implant has been manufactured by means of 3D printing, of a biocompatible material, preferably of titanium, tantalum or an alloy thereof. Said materials are highly suitable for subperiosteal implants but can be cut more easily than Vitallium. In the process of 3D printing the body can be manufactured such that the surfaces contacting bone tissue have a roughness or porosity, contrary to cast bodies, which is conducive to the process of adhesion to bone.

Subperiosteal jaw implants are made as one unity in a U-shape in top view, having an arc length adapted to the support length to be provided to the dental prosthesis or dentures. In case it regards dentures that have to extend over a large arc length, that means having to include teeth of both the group consisting of the right and left premolars and molars, in particular to include teeth of the group consisting of the right and left molars, the jaw implant that has a dimension corresponding with the number of pillars required for exo-prosthesis, will also have a large arc length.

Insertion of such a jaw implant may prove to be very difficult, or even impossible, if the patient's mouth opening is limited, for instance by nature, a birth defect, because of aging, or caused by trauma or as a result of maxillary joint pathology. A limited lip elasticity may also make insertion of the jaw implant more difficult. If insertion can take place successfully indeed, fixation of the implant will also prove difficult, and possibly not take place as it should be, as a consequence of which the end result will be below expectations and possibly require further medical procedures or restorative surgery.

In a further development according to the invention, which is elucidated below in connection with an assembly of the type mentioned in the preamble, this is improved upon because the jaw implant has been divided into bodies or segments that have been configured for respective placement in different areas of the alveolar ridge, spaced apart from each other in arc direction of the alveolar ridge.

At least one body or segment can be intended for supporting dentures, which
comprise at least a few of the group consisting of the right premolars and right molars and at least a few of the group consisting of the incisors, the canine, the premolars and the molars situated to the left of the median line
and/or
comprise at least a few of the group consisting of the left premolars and left molars and at least a few of the group consisting of the incisors, the canine, the premolars and the molars situated to the right of the median line.

At least one of the bodies or segments can be configured for placement on the alveolar ridge at the location of the right molars and/or left molars, and, in particular, be configured for placement at one side of the median line.

At least one of the bodies or segments can be configured for placement on the alveolar ridge at the location of incisors and/or a canine, and in particular, be configured for placement at one side of the median line.

The bodies or segments can be configured for placement on the alveolar ridge with intermediate distances from one to the other, so that intermediates spaces are situated in between them.

In a further development the body has been provided or the bodies have been provided with attachment holes for screws for attaching the implant to the jawbone. The attachment holes may have been provided on a second portion of the J-shaped, L-shaped or U-shaped body forming an upright leg thereof, in particular when the second portion has been formed for attachment to the buccal side of the jawbone in question. The screws can then find a reliable hold in the jawbone.

In one embodiment the body or segment has been provided with extensions, provided with one or more of the attachment holes. For an implant for the mandible, the body may have been provided with such an extension for attachment to the corpus mandibulae and/or with such an extension for attachment to the ramus ascendens mandibulae, in particular for attachment to the frontal edge (trigonum retromolare) of the ramus ascendens mandibulae, or lateral from the ascending branch of the mandible, dorsally extending, resulting in a high degree of stability. For an implant for the maxilla, the body can be provided with such an extension for attachment adjacent to the apertura piriformis and/or for attachment to the zygomatic pillar and/or the zygoma.

The optimal location and shape of the extensions can be determined by means of a scan of the jaw in question and the connecting bone areas.

In one embodiment the supporting areas at the convex side of the body have been provided with elevations which, at their end facing away from the body, have been provided with a means for attaching an exo-prosthesis thereto, either with or without the interposition of an intermediate pillar. The elevations, either with or without intermediate pillar, form support members for supporting the exo-prosthesis on the supporting areas of the body of the implant. The elevations preferably have been integrally formed with the body, so that discontinuities are kept within limits, and it is possible for them to be executed in said 3D print in accordance with the wanted design.

In one embodiment the elevations protrude from the body up to a distance that is sufficient for their circumferential surface to extend above the gingiva after having been placed. The circumferentially situated surfaces of the connection to a further part, such as an exo-prosthesis, placed on the elevation, will then remain above the gingiva thus reducing the risk of peri-mucositis and gingivitis. The elevations can be pillar-shaped and in one embodiment at their outer ends be provided with a means for direct attachment of an exo-prosthesis thereon. This can for instance be done by means of attachment means, such as screws, extending through the attachment holes in the exo-prosthesis and engaging in the outer end of the pillar-shaped elevations for attachment. An assembly according to the invention, in addition to the implant described, also comprises an exo-prosthesis and the means for attaching the exo-prosthesis to the implant, in particular pillar-shaped elevations.

At their outer ends the elevations can be provided with a means for attaching an intermediate pillar thereon, which intermediate pillar can extend to above the gingiva and at its opposite end has been provided with a means for attaching an exo-prosthesis thereon, either in the center line of the pillar or not. The connection intermediate pillar-exo-prosthesis can be as described in the previous paragraph.

According to a further aspect, the invention provides a method for manufacturing a subperiosteal implant according to any one of the preceding claims, wherein a 3D scan, in particular a CT scan or more in particular a CBCT scan is made of a jaw for which the implant is intended, on the basis of which scan a design of the implant is made, the design is entered as a CAD file into the operating system of a 3D printer which is fed with a bio-compatible printing material suitable for subperiosteal implants, after which the designed implant is printed by the 3D printer using the printing material, in accordance with the design in the CAD file. In that way a properly fitting implant can be manufactured in manner that will not inconvenience the patient.

In one embodiment of this method for manufacturing an implant as described above, wherein the supporting areas at the convex side of the body have been provided with elevations which at their end facing away from the body have been provided with a means for attaching an exo-prosthesis thereon, either with or without the interposition of an intermediate pillar, the elevations are provided in a number that is an excess of the required number. In that way the stability of the prosthesis is not put at risk when an elevation including optional intermediate pillar needs to be removed due to full-blown peri-implantitis.

According to a further aspect, the invention provides a method for intervening in cases of imminent onset of or full-blown peri-implantitis in the area of a support column forming the connection between a subperiosteal implant and an exo-prosthesis, wherein a relatively weakened area forming the connection between the support column in question and the concave body of the implant placed against the jawbone, is broken and the support column is removed. In one embodiment the exo-prosthesis is placed back again after removal of the elevation.

It is an object of the invention to provide an assembly of the type mentioned in the preamble that can also easily be placed in the above-mentioned difficult circumstances (in terms of introduction into the mouth, and such).

It is an object of the invention to provide an assembly of the type mentioned in the preamble that can also be reliably placed in the above-mentioned difficult circumstances.

It is an object of the invention to provide an assembly of the type mentioned in the preamble that can also be placed with overview in the above-mentioned difficult circumstances.

According to a further aspect the invention provides an assembly of
 a jaw implant for oral subperiosteal placement over the alveolar ridge of a patient's maxilla or mandible,
 dentures and
 supports for supporting the dentures on the jaw implant, spaced apart therefrom, which supports in particular form columns or pillars,
wherein the dentures comprise at least a few of the group consisting of the right premolars and right molars and at least a few of the group consisting of the incisors, the canine, the premolars and the molars situated to the left of the median line and/or comprise at least a few of the group consisting of the left premolars and left molars and at least a few of the group consisting of the incisors, the canine, the premolars and the molars situated to the right of the median line,
wherein the jaw implant has been divided into segments that have been configured for respective placement in different areas of the alveolar ridge, spaced apart from one another in arc direction of the alveolar ridge, and
wherein the dentures comprise a bridge part that is bending-rigid under the intended loads that occur and has an arc length that suffices to connect the segments to each other via the supports.

In that case the segments or bodies will have a size taking the limited mouth opening and/or limited lip elasticity into account and allowing to consecutively introduce them via the limited, existing mouth opening into the oral cavity. At that location they can be consecutively positioned, with overview, on the jawbone underneath the gingiva and other weak parts. Subsequently they can be connected to each other via the pillars and the bridge part continuing over the segments and forming a support for the dentures. The bridge part here forms a means for at least temporarily stabilizing the segments of the jaw implant, at least until the segments are/have been fixated to the jawbone using osteosynthesis screws. Placing those bone screws can also be executed reliably and with overview.

The invention enables nonetheless and reliably arranging a jaw implant, albeit in segments, for dentures spanning a considerable arc length, in an oral cavity of limited access. The dentures may have such an arc length as to comprise right molars and/or left molars, in particular second molars and more in particular third molars.

At least a few of the segments can each form a curved plate-shaped body which in cross-section, in the condition in which it has been placed on the alveolar ridge transverse to the alveolar ridge, has been formed concave towards the alveolar ridge, such as J-shaped, L-shaped or U-shaped, like a kind of full or semi saddle shape, wherein in or near a first portion forming the base of the body, in particular forming the base of the J, L or U, the body has been provided with one or more supporting areas for the (column-shaped) supports, which supporting areas have been integrally formed with the body. The body in question can be provided with holes for bone screws and with holes through which bone tissue can grow.

The stability of the segments or bodies can be enhanced if the bridge part and at least one of the segments or bodies have been configured for mutual connection by means of two or more of said supports. In a further embodiment thereof the bridge part and each of the segments have been configured for mutual connection by means of two or more of said supports.

Depending on the wanted procedure at least one of the segments can be configured for placement on the alveolar ridge at the location of the incisors and/or canine(s) and the dentures comprise related incisors and/or canine(s).

In one embodiment the segments have been configured for placement on the alveolar ridge at intermediate distances from each other. In that way more room is provided when placing a next segment on the alveolar ridge.

If the distance between maxillary alveolar ridge and mandibular alveolar ridge is sufficient the dentures can be configured as two-part supra structure, wherein the dentures comprise a continuous bridge part and a continuous dental part to be attached to the bridge part, which dental part comprises teeth of the group consisting of the premolars and molars and optionally teeth of the group consisting of incisors/canine(s). The bridge part then forms a retentive part of a second structure, which as visible dental part can then easily be placed inside and removed from the mouth, and then for instance be cleaned.

If the bite height is low it may be advantageous to configure the exo-prosthesis substantially as a one-part supra structure, wherein the dentures comprise a continuous bridge part and a dental part forming one unity therewith, which dental part comprises teeth of the group consisting of the premolars and molars and optionally teeth of the group consisting of incisors/canine(s).

For enhancing the stability, the connection between the bridge part and the column-shaped supports is angularly rigid under the intended conditions of use, and likewise the connection between each implant segment and the column-shaped supports in question is angularly rigid under the intended conditions of use.

At least one of the segments can be configured for placement on the alveolar ridge at the location of the right molars and/or left molars, and, in particular, be configured for placement at one side of the median line.

At least one of the segments can be configured for placement on the alveolar ridge at the location of incisors and/or canine(s), and in particular, be configured for placement at one side of the median line.

In one embodiment the jaw implant has been configured for placement on the alveolar ridge of the mandible. At least one of the segments can then be provided with an extension having holes for attachment to the corpus mandibulae and/or with an extension having holes for attachment to the ramus ascendens mandibulae, over the trigonum retromolare in the direction of the processus coronoideus, or lateral from the ascending branch of the mandible, dorsally extending.

In another embodiment the jaw implant has been configured for placement on the alveolar ridge of the maxilla. At least one segment can then be provided with an extension having holes for attachment adjacent to the apertura piriformis and/or with an extension having holes for attachment to the cheekbone (zygoma) or the zygomatic pillar (also bone area to the dorsal side of the fossa canina that is suitable for attachment).

These extensions augment the dimensions of the implant, which is not problematic because of the division into segments, which leaves sufficient room for placement. Screw fixation in the bone via the openings of the implant can take place via intra-oral or extra-oral (through the skin) access.

According to a further aspect, the invention provides a method for placing dentures in a patient's mouth, which dentures comprise at least a few of the group consisting of the right premolars and right molars and at least a few of the group consisting of the incisors, the canine, the premolars and the molars situated to the left of the median line and/or
comprise at least a few of the group consisting of the left premolars and left molars and at least a few of the group consisting of the incisors, the canine, the premolars and the molars situated to the right of the median line,
wherein the dentures comprise a bridge part formed as one unity and a dental part,
wherein an implant constituting of segments is made, with at least a segment for the right area of teeth of the group consisting of premolars and molars and/or at least a segment for the left area of teeth of the group consisting of premolars and molars, the segments are provided with supports, in particular column-shaped or pillar-shaped supports, for supporting the dentures, and the segments are successively placed on the prospective areas on the sufficiently exposed alveolar ridge, at least the bridge part is attached to the supports in order to form a connecting bridge between the placed segments, the segments are attached to permanent jaw material, in particular by means of bone screws, the gingiva is placed back again, over the segments, and is sutured.

Because the segments have not yet been fixated to the jawbone when placing either the bridge part of the dentures, or the complete dentures, the precise attachment of the bridge part et cetera to the supports is facilitated and enhanced. The segments then still have some freedom to adapt themselves to the orientation imposed by the bridge part to the supports, such as columns.

In a first embodiment, dentures are placed comprising a bridge part formed as one unity and a dental part to be attached thereto, wherein first the bridge part is attached to the supports of all segments and subsequently the dental part is attached to the bridge part.

In a second embodiment, dentures are placed comprising a bridge part and a dental part that forms one unity therewith, so that placing the bridge part also includes placing the dental part.

In a further development also a segment for an area of incisors and/or canine(s) is being placed.

In a further development the segments are placed at intermediate distances from each other.

In one embodiment the (precision) attachment between bridge part and supports is realized by a screw fixation in or to columns or pillars present on the subperiosteal implant segment in question. In another embodiment other precision attachments are used, such as tongue-in-groove, Dalbo, Locators, rail mechanisms and connections known in for instance timber construction.

In another embodiment said precision attachments are realized in 3D-print/CNC connections between the subperiosteal segments at crest height.

According to a further aspect, the invention provides a subperiosteal implant to be placed on the alveolar ridge of a mandible or maxilla, wherein the implant has been divided into segments in alveolar ridge direction, in particular apparently suitable and intended for an assembly according to the invention.

According to a further aspect, the invention provides a jaw implant for oral, subperiosteal placement over the alveolar ridge of the maxilla or of the mandible, wherein the implant forms a body which in cross-section, in the condition in which it has been placed on the alveolar ridge transverse to the alveolar ridge, has been formed concave towards the alveolar ridge, such as J-shaped, L-shaped or U-shaped, wherein the body has been provided with one or more supporting areas for support members, such as pillars, for extending through the gingiva, in particular passing through it, said supporting areas being integrally formed with the body, said support members forming a support for an exo-prosthesis, such as a dental prosthesis or dentures, wherein the body extends over a part of the alveolar ridge only and has been provided with lips or extensions, which have been provided with one or more attachment holes for attachment to the bone.

If the body has been configured for placement on the mandible, it can be provided with such an extension for attachment to the corpus mandibulae and/or with such an extension for attachment to the ramus ascendens mandibulae, in particular for attachment to the frontal edge (trigonum retromolare) of the ramus ascendens mandibulae, over the trigonum retromolare in the direction of the processus coronoideus, or lateral from the ascending branch of the mandible, dorsally extending.

If the body has been configured for placement on the maxilla, it can be provided with such an extension for attachment adjacent to the apertura piriformis and/or be provided with such an extension for attachment to the zygomatic pillar and/or the zygoma.

The body can be configured for placement at one side of the median line only. The body can be configured as discussed above in the assembly according to the invention.

The aspects and measures described in this description and the claims of the application and/or shown in the drawings of this application may where possible also be used individually. Said individual aspects may be the subject of divisional patent applications relating thereto. This particularly applies to the measures and aspects that are described per se in the sub claims.

BRIEF DESCRIPTION OF THE DRAWINGS

The invention will be elucidated on the basis of a number of exemplary embodiments shown in the attached drawings, in which.

DETAILED DESCRIPTION OF THE DRAWINGS

Figure 1:
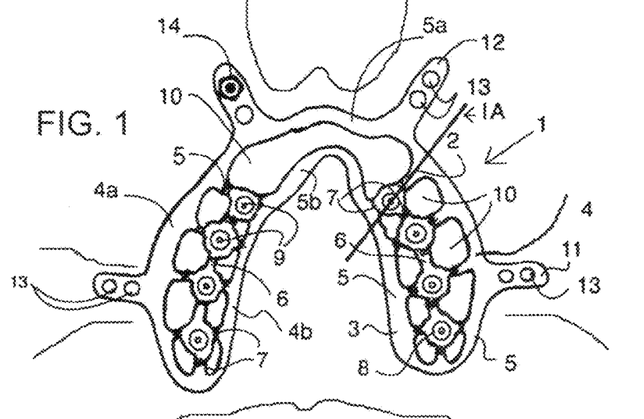
FIG. 1 shows a bottom view of a jaw implant according to the invention placed on a maxilla.

The subperiosteal jaw implant 1 of FIG. 1 has been placed against the alveolar ridge of the maxilla. For reasons of an illustrative nature, the implant 1 is shown folded out slightly flat. The implant 1 is formed by a body 2 formed as one unity of titanium or tantalum, or an alloy thereof.

Figures 1A, 2, 2A:
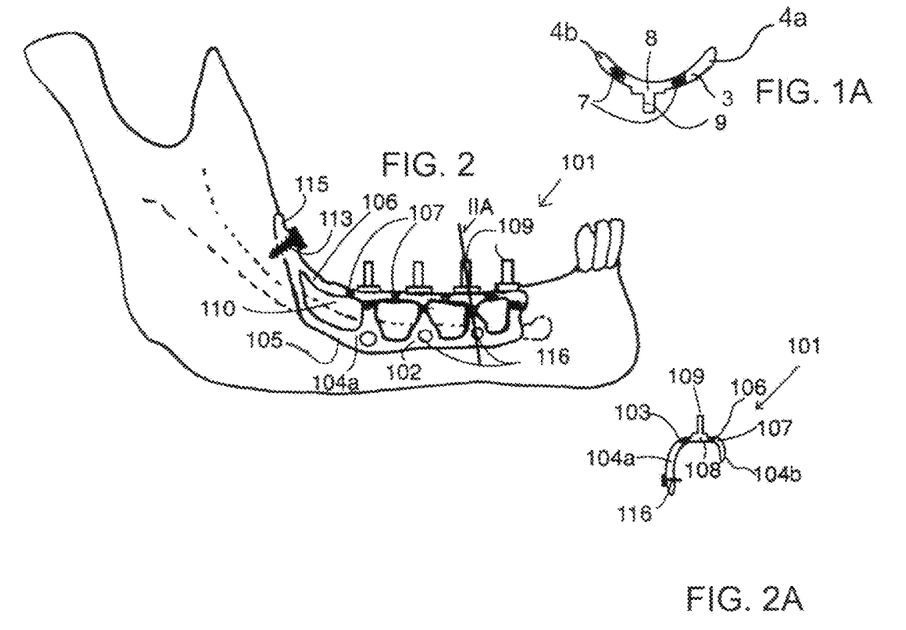
FIG. 1A shows a vertical cross-section of the implant of FIG. 1, according to plane 1A.
FIG. 2 shows a side view of a jaw implant according to the invention placed on a mandible.
FIG. 2A shows a vertical cross-section of the implant of FIG. 2, according to plane 2A.

As can be seen in the cross-section of FIG. 1A, the body 2 has a gentle U-shape having a portion 3 abutting the crest of the alveolar ridge and portions 4a, 4b that are formed as one unity therewith and abut the palatal (palate) sides and the buccal (cheek) and labial (lip) sides, respectively, of the alveolar ridge. The implant 1 can for instance have an arc length suitable for dentures having teeth of the group consisting of the right premolars and molars and teeth of the group consisting of the left premolars and molars. The body 2 is frame-shaped or grid-shaped, having main bars or main strips 5, 5a, 5b, that are circumferential, and auxiliary bars or auxiliary strips 6. The bars 5a and 5b are intended to abut the labial and the palatal sides, respectively, of the alveolar ridge. Spacious holes 10 through which tissue can grow have been left open between the bars 5, 5a, 5b and bars 6. Supporting areas 8, in this case having integrally formed column-shaped elevations 9 for connection to an exo-prosthesis that is not shown, are surrounded by holes 10 and are connected to the rest of the body by the bars 6 only. Weakenings 7 (as discussed above) have been formed in the material of the body, approximately halfway the bars 6. Each column 9 therefore has its own supporting area 8, which has been provided with a weakening 7 in each connection 6 to the rest of the body 2.

The body 2 has furthermore been provided with integrally formed attachment lips 11 and 12, which have been provided with attachment holes 13 for osteosynthesis screws 14. The lips 11 are intended/configured for attachment to zygomatic pillars, the lips 12 are intended/configured for attachment to the bone adjacent to the apertura piriformis.

In FIG. 2 a subperiosteal jaw implant 101 has been placed against the left alveolar ridge of the mandible. The implant 101 is formed by a body 102 formed as one unity of titanium or tantalum, or an alloy thereof.

As can be seen in the cross-section of FIG. 2A, the body 102 is U-shaped having a portion 103 abutting the crest of the alveolar ridge and two pending portions 104a,b formed as one unity therewith, which portions abut the buccal and lingual sides, respectively, of the left alveolar ridge. The body 102 is grid-shaped, having main bars or main strips 105 that are circumferential, and auxiliary bars or auxiliary strips 106. Holes 110 through which tissue can grow, have been left open between the bars 105 and the bars 106. Supporting areas 108 having integrally formed supports 109 for columns or pillars that have not been shown, for an exo-prosthesis are surrounded by holes 110 and are connected to the rest of the body by the bars 106 only. The bars 106 have been formed with weakenings 107 in the material of the body.

The body 102 has furthermore been provided with integrally formed attachment lip 115, which has been provided with attachment holes 113 for osteosynthesis screws 114. The lips 115 are intended/configured for attachment to the frontal edge (trigonum retromolare) of the ramus ascendens mandibulae. Portion 105a has been provided with attachment holes 116, also for osteosynthesis screws 114.

Figure 3:
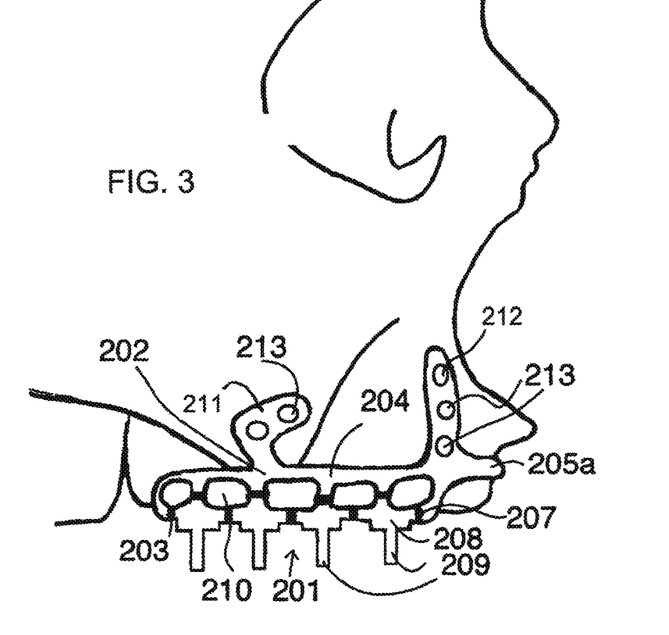
FIG. 3 shows a side view of an implant according to the invention placed on a maxilla.

FIG. 3 shows another embodiment of a subperiosteal jaw implant 201 for a maxilla. Parts that are similar to the implant 1 of FIG. 1 have the same reference numbers increased by 200. Lip 211 is for attachment to the zygomatic pillar and lip 212 is for attachment to the bone adjacent to the apertura piriformis.

Figure 4:
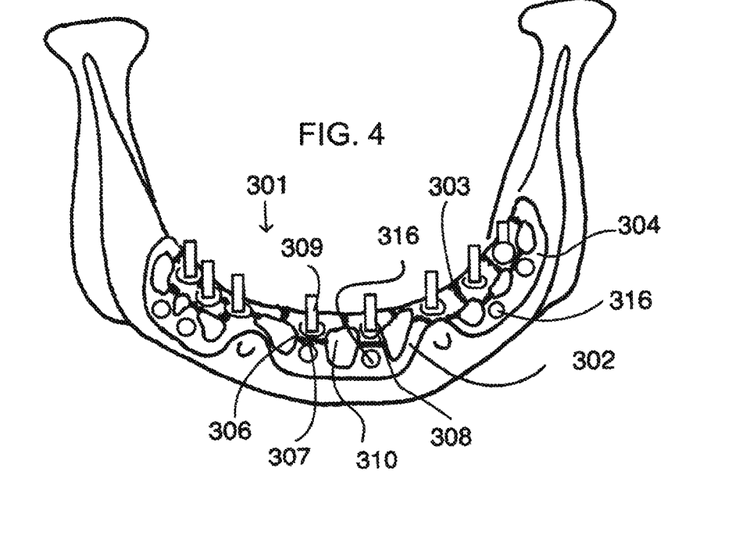
FIG. 4 shows an oblique top/front view of an implant according to the invention placed on a mandible.

FIG. 4 shows another embodiment of a subperiosteal jaw implant 301 for a mandible. Parts that are similar to the implant 101 of FIG. 2 have the same reference numbers increased by 200. The implant 301 has been formed like a continuous body 302 to be placed on both sides of the jaw and the portion situated in between. Attachment holes 316 have been provided for osteosynthesis screws for attachment.

Figure 5A:
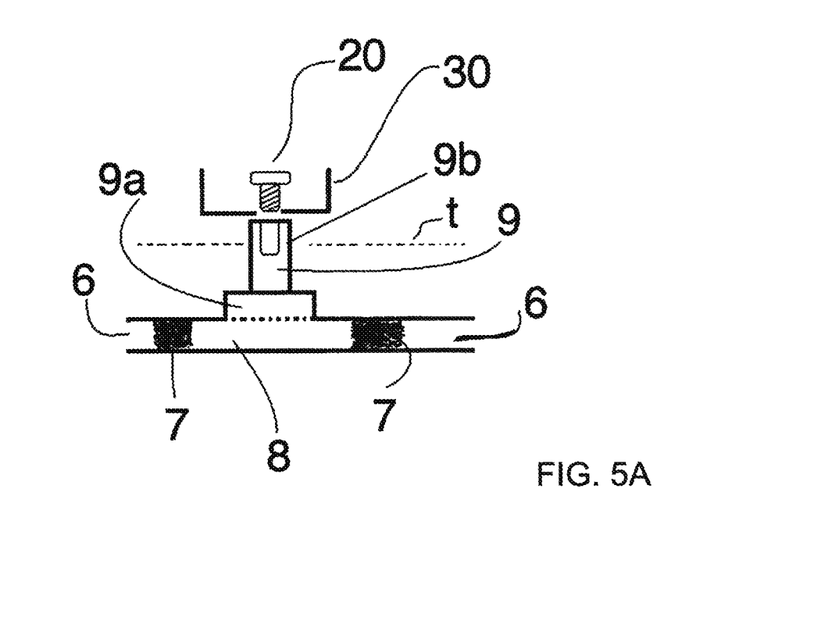
FIGS. 5A and 5B show examples of a pillar structure in an assembly of a jaw implant according to the invention and a prosthesis.

FIG. 5A schematically shows an example of attaching an exo-prosthesis to an example of an implant according to the invention. The column-shaped elevation 9 forms a support member for an exo-prosthesis and is step-shaped having a foot 9a and a column 9b, which has such a length as to extend above the crest t of the gingiva. In the upper end the column 9b has been provided with a bearing surface which has a screw hole in there for screw 20 in order to secure prosthesis 30.

Figure 5B:
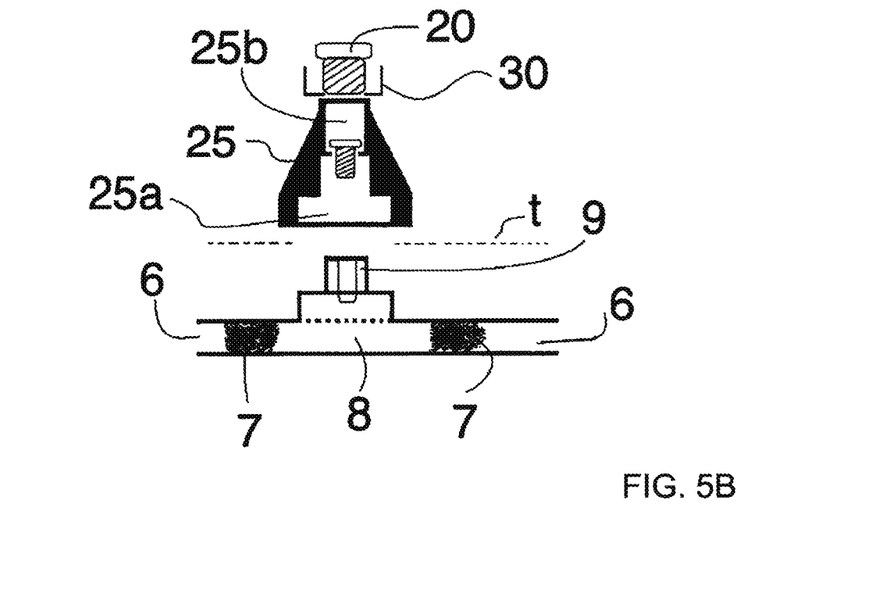

In FIG. 5B the elevation 9 is narrower and shorter, and extends to below the crest t of the gingiva. For supporting dentures at the correct height, an intermediate pillar 25 has been placed on the elevation 9. In its lower side the intermediate pillar 25 has been provided with an accommodation space 25a in order for it to fit on the elevation 9 therewith and to be secured thereto by means of a screw. In the upper side the intermediate pillar has been provided with a screw hole 25b for screw 20 in order to secure prosthesis 30. Here, the prosthesis is attached indirectly to the elevation 9 on a support member that is composed of elevation 9 and intermediate pillar 25.

The embodiment of FIG. 5A has the advantage of a transition in the exterior surface situated below the crest of the gingiva being absent, thus reducing the risk of contamination.

The implant is placed in the patient by exposing the alveolar ridge by making a few incisions in the gingiva. The implant is placed on the alveolar ridge and attached to permanent jaw material using osteosynthesis screws. The gingiva is placed back again over the implant and sutured. The columns extend to above the gingiva.

Finally, the exo-prosthesis is placed on the columns.

After a while the implant will get osseointegrated with the bone membrane and with the gingiva. If the weakened areas 7, 107, 207, 307 have been formed by an incision at the bone side or have a porous surface at that location, this will be conducive to osseointegration. The forces resulting from chewing motions can be absorbed by the jaw via the various screw attachments. The motions of the implant relative to the gingiva and bone membrane will then remain within limits.

If a column extending through the gingiva has a mechanical problem or when there is question of peri-mucositis at said column, it is possible, after having detached the exo-prosthesis and cutting the gingiva around the column in question open in flaps, to detach the column 9 including its supporting area 8 from the body 2 of the subperiosteal implant 1, 101, 201, 301 through a machining action at the location of the weakened areas 7, 107, 207, 307. In case the body has been made of titanium or tantalum, or an alloy thereof, the machining action can be executed more easily than would be the case with the chromium-cobalt-molybdenum type alloys.

It is noted that the columns 9 can alternatively be executed as separate elements, and are then securely attached to the supporting areas 8, et cetera, inseparable therefrom.

Manufacturing using 3D printing enables shaping the weakenings in any wanted way, such as by porous areas, for instance with pores having a maximum cross-section of 0.5 mm, hollow areas, incisions, or perforations having a diameter that is smaller than the thickness of the body at that location.

Figures 6A, 6B:
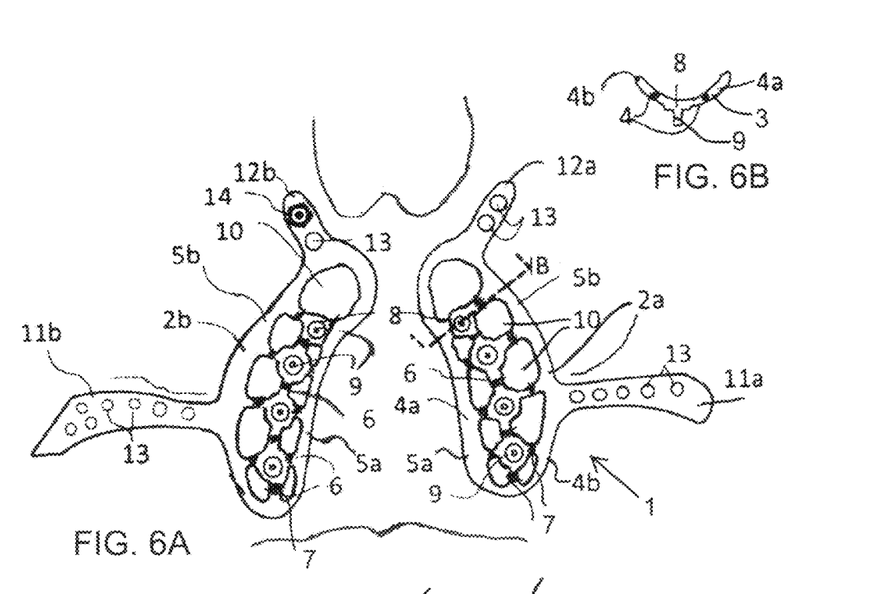
FIG. 6A shows a bottom view of a jaw implant according to the invention placed on a maxilla.
FIG. 6B shows vertical cross-section of the implant of FIG. 1, according to plane 6B.

FIG. 6A shows a jaw implant 1 according to the invention, divided into segments, placed against the alveolar ridge of the maxilla. For reasons of an illustrative nature, the implant segments or bodies 2a,b are shown folded out slightly flat, just like in FIG. 1. The implant segments or bodies 2a,b have been formed as one unity per se, made of titanium or tantalum, or an alloy thereof.

As can be seen in the cross-section of FIG. 6B, the bodies 2a,b are slightly U-shaped having a portion 3 abutting the crest of the alveolar ridge and portions 4a, 4b that are formed as one unity therewith and abut the palatal (palate) sides and the buccal (cheek) and labial (lip) sides, respectively, of the alveolar ridge. The bodies 2a,b are frame-shaped or grid-shaped, having main bars or main strips 5, 5a, 5b that are circumferential, and auxiliary bars 6. The bars 5a and 5b are intended to abut the respective palatal sides of the alveolar ridge. Holes 10 through which tissue can grow have been left open between the bars 5, 5a, 5b and bars 6. Supporting areas 8, in this case having integrally formed column-shaped elevations 9 that are connected thereto in an angularly rigid manner, for an exo-prosthesis that is not shown yet (see FIG. 6C), are surrounded by holes 10 and are connected to the rest of the body by the bars 6 only. Each column 9 therefore has its own supporting area 8.

Like in the preceding examples, weakenings 7 have been formed in the material of the body approximately halfway the bars 6, in accordance with what has been discussed above. Each column 9 therefore has its own supporting area 8, which has been provided with a weakening 7 in each connection 6 to the rest of the body 2.

Figure 6C:
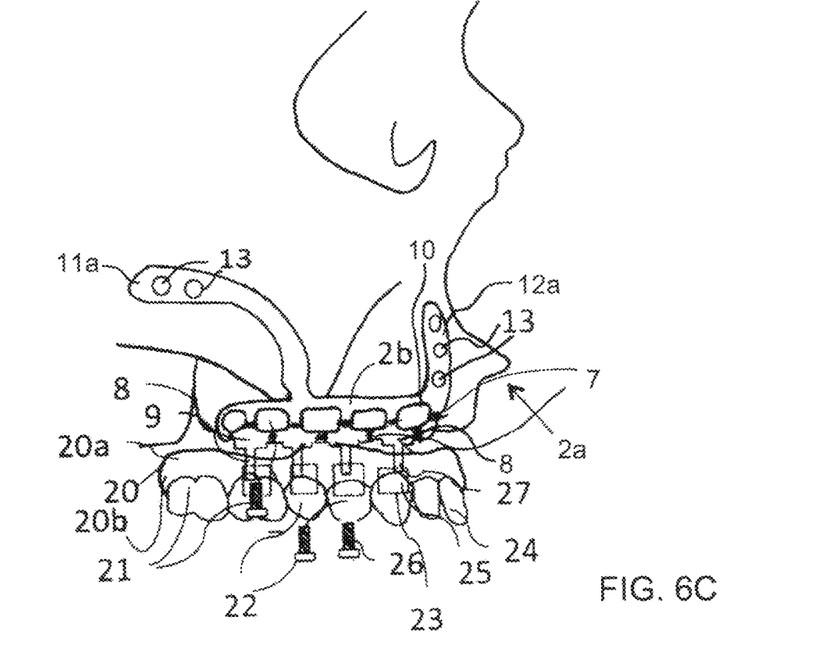
FIG. 6C shows a side view of an assembly according to the invention with a segment of the jaw implant according to FIG. 6A.

The bodies 2a,b have furthermore been provided with integrally formed attachment lips 11 and 12, which have been provided with holes 13 for osteosynthesis screws 14. The lips 11 are intended for attachment to the zygomatic pillars and the zygoma, the lips 12 for attachment adjacent to the apertura piriformis. In FIG. 6C the lips have been executed slightly different from those in FIG. 6A.

Prior to placing the segments 2a,b the alveolar ridge has been exposed by making a few incisions in the gingiva. Despite the presence of the rather long extensions 11 and 12, the segments 2a,b have in a controlled manner been successively introduced into the patient's mouth, and placed at the correct location on the maxillary alveolar ridge. See FIG. 6C for segment 2a. If so desired, the segments 2a,b can be kept in their place for the time being using a few temporary screws. These screws only need to be put in a number of places and can be shorter than the osteosynthesis screws that will ultimately be placed.

Then the dentures 20 can be placed. In FIG. 6C the dentures are substantially one-part, having a base part 20a made of metal forming a bending-rigid bridge part continuing in dental arc direction/alveolar ridge direction, and a dental part 20b in polymer or PMMA modelled thereon having molars 21, premolars 22, canines 23 and incisors 24. The dentures comprise teeth of the group consisting of the premolars and molars and extend on both sides of the median plane M. The bridge part 20a has been provided with holes 27 for snugly fitting accommodation of the outer ends of columns 9, and the dental part 20b has been provided with holes 25 for entry of screws 26 the screw thread of which engages with the screw thread in the columns 9. The head of the screw 26 fits into the hole 25, wherein in the bottom of the hole 25 is an opening to the hole 27 for fitting passage of the screw shank. The screws 26 create an angularly rigid connection of bridge part 20a to segments 2a,b. The holes 25 are filled later on by a suitable filler.

The bridge part 20a then connects both segments 2a,b rigidly, wherein the stability of the segments is enhanced, which is advantageous for fixating the segments after that.

Subsequently the segments 2a,b are permanently fixated at intermediate distance from one another, to the labial/ buccal side of the maxillary alveolar ridge using osteosynthesis screws 14, and are also attached to the zygomatic pillar and adjacent to the apertura piriformis using the osteosynthesis screws 14. The gingiva is placed back again, around the columns 9 and over the implant, and sutured. The columns 9 extend to above the gingiva.

Figures 7A, 7B, 7C, 7D:
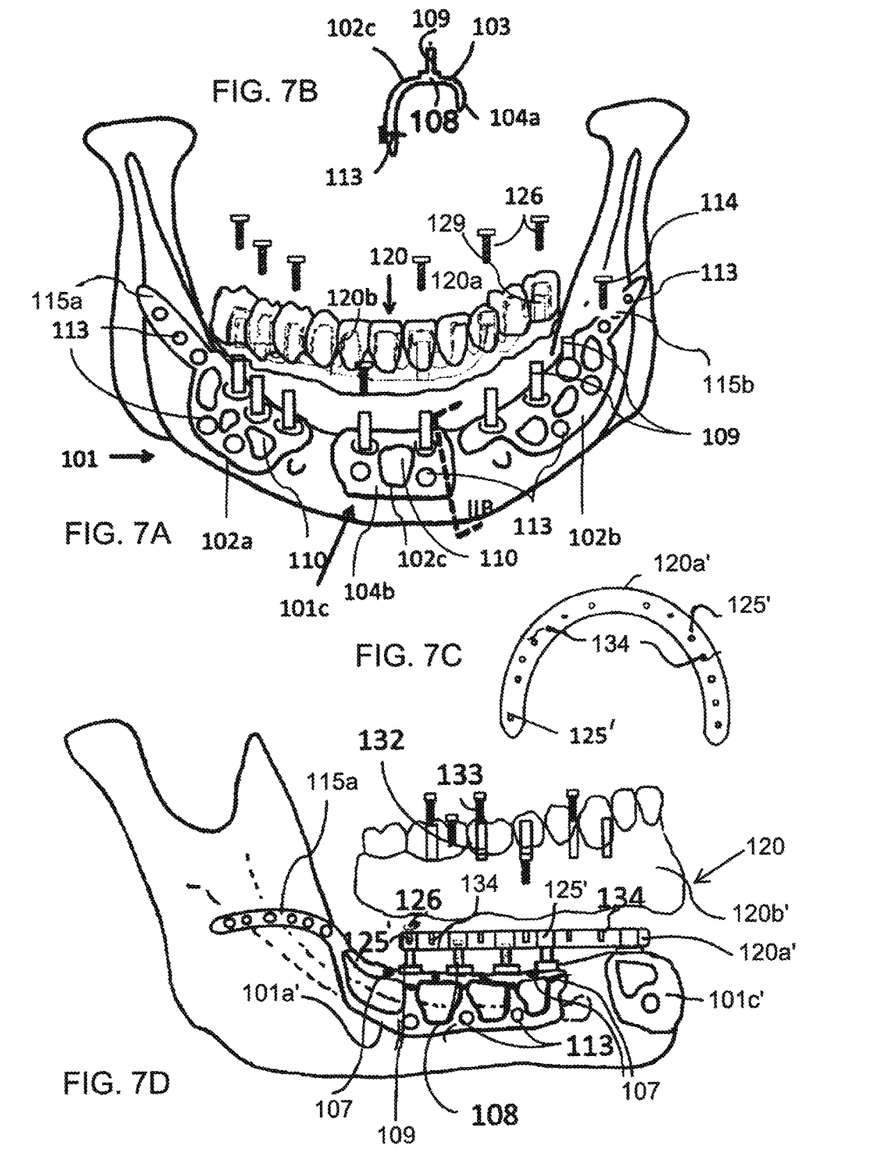
FIG. 7A shows an oblique top/front view of an assembly according to the invention placed on a mandible.
FIG. 7B shows a vertical cross-section of a segment of the implant of the assembly of FIG. 7A, according to plane 7B.
FIG. 7C shows a top view of a bridge part of two-part dentures for an assembly according to the invention that slightly differs from FIG. 7A for a mandible, like in FIG. 7D.
FIG. 7D shows a side view of an assembly according to the invention for a mandible.

In FIG. 7A a subperiosteal jaw implant 101 has been placed against the mandible. The implant 101 is constituted of three segments or bodies 102a-c each formed as one unity made of titanium or tantalum, or of an alloy thereof.

As can be seen in the cross-section of FIG. 7B for segment or body 102c, each segment or body 102a-c is U-shaped having a portion 103 abutting the crest of the alveolar ridge and two pending portions 104a,b that are formed as one unity therewith, and abut the labial and lingual sides, respectively, of the alveolar ridge or, for bodies 102a,b, abut the buccal and lingual sides of the left and right alveolar ridge. The bodies 102a-c are grid-shaped, having holes 110 through which tissue can grow and screw holes 113 for osteosynthesis screws 114 and with supporting areas 108 having integrally formed columns 109 for an exo-prosthesis in the form of dentures 120.

The segments or bodies 102a,b have furthermore been provided with integrally formed attachment lips or extensions 115a,b that have been provided with holes 113 for osteosynthesis screws 114. The lips 115a,b are intended for attachment to the lateral side of the ramus ascendens mandibulae, dorsally extending.

Despite the rather long extensions 115a,b, the segments or bodies 102a,b have in a controlled manner been successively introduced into the patient's mouth and placed at the correct location on the alveolar ridge. If so desired, the segments 102a,b could be kept in their place for the time being using a few temporary screws. After this has successively been done for both, the segment 102c is placed, optionally also by means of a temporary screw, in order to realize the situation of FIG. 2A, in which the segments are situated at intermediate distances from each other.

In this example the dentures 120 to be placed are one-part like in FIG. 7C, that means that the bridge part 120a and dental part 120b form one unity with each other and therefore are placed as a unit. The dentures 120 comprise teeth of the group consisting of the premolars and molars and extend on both sides of the median plane M. The dental part 120b with the teeth (premolars/molars and incisors/canine(s)) is made of polymer or PMMA. Downwardly oriented holes or accommodation spaces 127 are present in the metal bridge part 120a for snugly fitting accommodation of the columns 109. While placing the dentures on the columns 109, the holes 127 are able, if necessary, to orient the columns 109 and thus the segments that are rigidly connected to the columns. Holes or accommodation spaces 125 have been arranged in the upper side of the dentures 120, in which holes or accommodations spaces screws 126 are inserted and via a hole in the bottom of said holes can be screwed into the columns 109 in order to fixate the bridge part 120a and thus the dentures 120 and the segments to each other.

The screws 126 now also realize an angularly rigid connection of bridge part 120a to the segments 102a, 102b and 102c. The holes 125 are filled later on by a suitable filler.

The bridge part 120a then rigidly connects the three segments or bodies 102a,b,c, thus enhancing the stability of the segments placed on the alveolar ridge, at least until they have been fixated to the lateral side of the ramus ascendens mandibulae and to the alveolar ridge using osteosynthesis screws 114 in all holes 113. The gingiva can subsequently be placed back again and sutured.

In FIGS. 7C and 7D the embodiment is slightly different. The segment 102c extends onwards along the alveolar ridge to the left side. Furthermore, the dentures 120' are two-part, in this case having a separate bridge part 120a' and a separate dental part 120b, to be placed successively. As can also be seen in top view in FIG. 7C, the bridge part 120a' at the side of the dental part 120b' has been provided with two types of holes, namely holes or accommodation spaces 125' for screws 126' with which the bridge part 120a' can be screwed onto the columns 109', and holes 134 for screws 133 with which the dental part 120b' can be screwed onto the bridge part 120a'.

The way of placement largely corresponds with placing the assembly of FIG. 7A, however, not until after the bridge part 120a itself has been fixated to the columns 109' and the segments have been fixated to the alveolar ridge using osteosynthesis screws 114, will the dental part 120b' be detachably attached to the bridge part 120a' using the screws 133 that can be inserted into the holes/accommodation spaces 132 in the dental part 120b' for screw engagement into the holes 134.

After a while the implant segments will get osseointegrated with the bone membrane and with the gingiva. Until that time the bridge part ensures stabilization of the segments.

In one embodiment each segment has been provided to be ideally positioned by means of the precision attachment between the subperiosteal segments and the supra structure, which spatially define the segments in their ideal configuration relative to each other and relative to the jawbone.

Manufacturing the implants according to the invention, either in the segmented embodiment or not, can take place as follows. The patient is in need of an exo-prosthesis, yet due to an atrophied jawbone they have insufficient material to attach and anchor endosseous implants. Bone reconstruction using the patient's own bone or donor bone or using synthetic bone is not an option and neither is bone grafting. In such cases a subperiosteal implant may be the solution.

A three-dimensional image is made of the jaw or the jaw part in question of the patient's, which reveals the specific contours and condition of the jawbone. This is done using a 3D scanner, in particular a CT scanner, more in particular a CBCT scanner.

The 3D image is stored and made available to a designer of subperiosteal implants. The designer designs an optimal design of the subperiosteal implant for the patient using a CAD program. The designer then also decides on the locations of attachment by means of screws and the design of the weakenings and/or the division into segments. The scan also provides information about the locations where the bone is sufficiently thick to serve as location of attachment. Based on the scan, the designer is able to decide on the use of, the location and the shape of extensions/lips.

The design can be stored in a design file suitable for operating a 3D printer. The 3D printer in configured for printing medical implants made of biocompatible materials such as titanium or tantalum or alloys thereof.

The operating system of the 3D printer reads the design file and has the 3D printer print the body or the bodies in accordance with the design. The body obtained then forms the subperiosteal implant or the bodies obtained together form the subperiosteal implant constituting of segments. If required the body or the bodies/segments can be further finalized (such as finishing the threading), for instance in a CNC process.

The above description is included to illustrate the operation of preferred embodiments of the invention and not to limit the scope of the invention. Starting from the above explanation many variations that fall within the spirit and scope of the present invention will be evident to an expert.

The invention claimed is:

1. A jaw implant for oral, subperiosteal placement over an alveolar ridge of a maxilla or of a mandible,
   wherein the implant forms a body which, when placed on the alveolar ridge transverse to the alveolar ridge, has a cross section that is concave towards the alveolar ridge,
   wherein in or near a first portion forming a base of the body, the body comprises supporting areas for support members for extending through the gingiva, said supporting areas being integrally formed with the body, and said support members forming a support for an exo-prosthesis
   wherein the supporting areas are connected to the rest of the body via relatively weakened areas of the body only, said relatively weakened areas being weak as compared to the areas of the body connecting thereto, and
   wherein the body has an open structure that is a framework or grid, with bars surrounding holes of the open structure.

2. The jaw implant according to claim 1,
   wherein each supporting area is connected to the rest of the body via its own weakened areas.

3. The jaw implant according to claim 1,
   wherein the weakened areas are restricted to within the bars of the open structure.

4. The jaw implant according to claim 1,
   wherein the relatively weakened areas are formed by porous areas, wherein the pores have a cross-section that is smaller than 1 mm.

5. The jaw implant according to claim 1,
   wherein the weakened areas are formed by hollow bar sections or hollow strip sections.

6. The jaw implant according to claim 1,
   wherein the relatively weakened areas are formed by areas having a relatively reduced wall thickness.

7. The jaw implant according to claim 1,
   wherein the relatively weakened areas are formed by areas having perforations in the material of the body, and
   wherein the perforations have a cross-section that is smaller than the thickness of the body at that location.

8. The jaw implant according to claim 1,
   wherein the jaw implant is manufactured by 3D printing, and is made of titanium, tantalum or an alloy thereof.

9. The jaw implant according to claim 1,
   wherein the supporting areas at the convex side of said body comprise elevations which, at their end facing away from the body, comprise means for attaching an exo-prosthesis thereto, either with or without the interposition of an intermediate pillar, wherein the elevations have been integrally formed with said body.

10. The jaw implant according to claim 9,
    wherein the elevations protrude from said body up to a distance that is sufficient for their circumferential surface to extend above the gingiva after having been placed.

11. The jaw implant according to claim 9,
    wherein the elevations are pillar-shaped and their outer ends comprise means for direct attachment of an exo-prosthesis thereon.

12. The jaw implant according to claim 11,
    wherein outer ends of the elevations comprise means for attaching an intermediate pillar thereto, and
    the intermediate pillar, at its opposite end, comprises means for attaching an exo-prosthesis thereon.

13. A method for manufacturing the subperiosteal jaw implant according to claim 1,
    wherein
    a scan is made of a jaw for which the implant is intended, on the basis of which scan a design of the implant is made,
    the design is entered as a CAD file into the operating system of a 3D printer which is fed with a bio-compatible printing material suitable for subperiosteal implants,
    after which the designed implant is printed by the 3D printer using the printing material, in accordance with the design in the CAD file.

14. The method according to claim 13,
    wherein the supporting areas at the convex side of said body have been provided with elevations which, at their end facing away from the body, have been provided with a means for attaching an exo-prosthesis thereto, either with or without the interposition of an intermediate pillar, wherein the elevations have been integrally formed with the body in question, and
    wherein the elevations are provided in a number that is an excess of the required number for the attachment of the exo-prothesis.

15. The method according to claim 1,
    wherein the base of the body has been has been provided with at least three of said supporting areas.

16. The method according to claim 1,
    wherein the body has been provided with extensions, said extensions being provided with attachment holes for screws for attaching the implant to the jawbone on the exterior side of the jawbone.

17. The jaw implant according to claim 16,
    wherein the body is configured for placement on the mandible, said extensions comprising an extension for attachment to the corpus mandibulae and/or an extension for attachment to the ramus ascendens mandibulae, for attachment to the frontal edge (trigonum retromolare) of the ramus ascendens mandibulae, over the trigonum retromolare in the direction of the processus coronoideus, or lateral from the ascending branch of the mandible, dorsally extending.

18. The jaw implant according to claim 16,
    wherein the body is configured for placement on the maxilla,
    said extensions comprising an extension for attachment adjacent to the apertura piriformis and/or an extension for attachment to the zygomatic pillar and/or the zygoma.

19. The method for intervening in cases of imminent onset of or full-blown peri-implantitis in the area of a support column forming the connection between a subperiosteal jaw implant and an exo-prosthesis,
    wherein a relatively weakened area integral with the implant and forming the connection between the support column in question and a concave body of the implant placed against the jawbone is broken and the support column is removed.

20. The method according to claim 19,
    wherein the exo-prosthesis is placed back again after removal of the support column.

* * * * *